(12) United States Patent
Mitchell et al.

(10) Patent No.: US 6,270,727 B1
(45) Date of Patent: Aug. 7, 2001

(54) ANALYTICAL CRUCIBLE

(75) Inventors: Joel C. Mitchell, Bridgman; James L. French, Holland, both of MI (US)

(73) Assignee: Leco Corporation, St. Joseph, MI (US)

( * ) Notice: Subject to any disclaimer, the term of this patent is extended or adjusted under 35 U.S.C. 154(b) by 0 days.

(21) Appl. No.: 09/127,224

(22) Filed: Jul. 31, 1998

(51) Int. Cl.$^7$ ........................................................ B01L 3/00
(52) U.S. Cl. ................................................. 422/102; 422/99
(58) Field of Search ........................................ 422/99, 102

(56) References Cited

U.S. PATENT DOCUMENTS

| | | |
|---|---|---|
| 1,743,803 | 1/1930 | Arensberg et al. . |
| 2,930,602 | 3/1960 | Rohn . |
| 3,100,155 * | 8/1963 | Wagner .................... 106/62 |
| 3,281,596 | 10/1966 | Williston . |
| 3,403,982 | 10/1968 | Fricioni . |
| 3,619,839 | 11/1971 | Kraus et al. . |
| 3,650,823 | 3/1972 | Mead et al. . |
| 3,824,016 | 7/1974 | Woodriff et al. . |
| 3,899,627 | 8/1975 | Sitek et al. . |
| 4,091,970 | 5/1978 | Komiyama et al. . |
| 4,303,615 | 12/1981 | Jarmell et al. . |
| 4,328,386 | 5/1982 | Bredeweg .................... 373/118 |
| 4,573,910 | 3/1986 | Bredeweg . |
| 4,789,140 | 12/1988 | Lirones . |
| 5,064,617 | 11/1991 | O'Brien et al. . |
| 5,085,582 | 2/1992 | Edler . |
| 5,236,353 | 8/1993 | Adani et al. . |
| 5,246,667 | 9/1993 | Hemzy et al. . |
| 5,637,809 | 6/1997 | Traina et al. . |

FOREIGN PATENT DOCUMENTS 4104049   4/1992   (JP) .

OTHER PUBLICATIONS

Aldrich Catalog 1988, pp. 1942–1946.*

* cited by examiner

*Primary Examiner*—Arlen Soderquist
(74) *Attorney, Agent, or Firm*—Price, Heneveld, Cooper, DeWitt & Litton

(57) ABSTRACT

An analytical crucible is made of a ceramic material with openings to allow the escape of gaseous byproducts of combustion through the crucible while holding the sample. In a preferred embodiment, the crucible is made of a porous ceramic material having a mean pore diameter of from about 150 to 350 microns. The porous ceramic crucible is manufactured of a mixture of at least about 92% alumina and about 7.5% silica. In one embodiment, the crucible is generally cup-shaped.

17 Claims, 1 Drawing Sheet

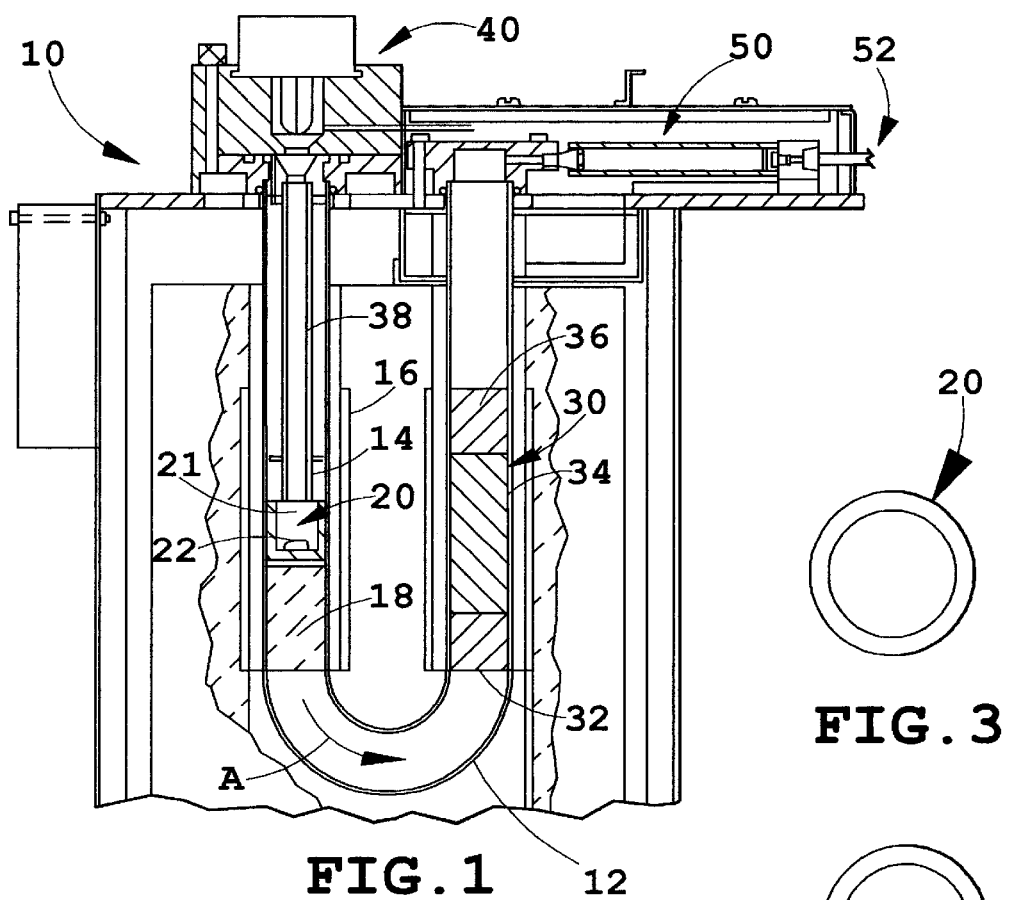
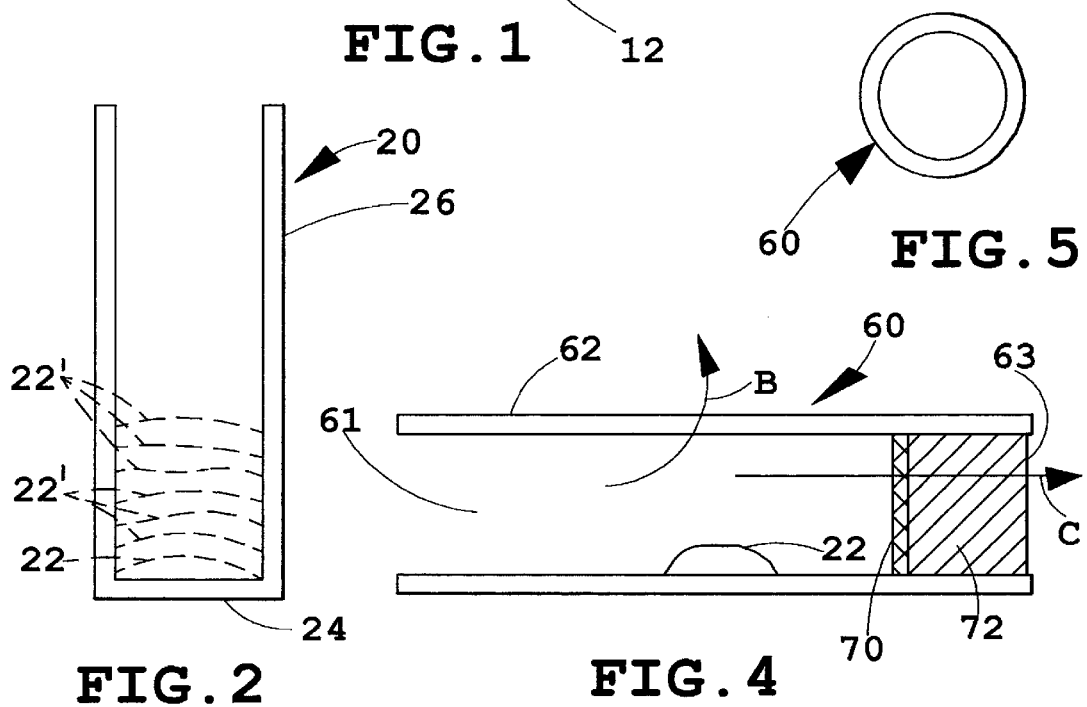

ANALYTICAL CRUCIBLE

BACKGROUND OF THE INVENTION

The present invention relates to crucibles for fusion of a specimen for analysis and particularly to a porous ceramic crucible.

Analyzers for the determination of elements such as carbon, nitrogen, hydrogen, oxygen, sulfur or other substances, such as protein, rely upon the combustion of a weighted quantity of a sample in a gas flow-through system for determining the byproducts of combustion. The gases are passed through absorption and purification stages and supplied to an analyzer to measure the resultant elements of interest. One such analyzer is disclosed in U.S. Pat. No. 4,573,910 assigned to the present assignee. Typically, such analyzers integrally include a furnace which may be a resistance furnace, induction furnace or other type furnace which heats a specimen within a crucible to combustion temperatures in the range of 1000° C. To assist in complete combustion, typically a lance tube is employed and directs a carrier gas into the open mouth of the crucible during heating to facilitate combustion of the sample. The gaseous byproducts of combustion subsequently flow around the outer periphery of the lance tube and/or crucible into the analyzer from the furnace.

The difficulty with such system is that the crucibles frequently can only be used for approximately 40 to 80 analyses. Accordingly, there exists a need for a crucible which not only can be used repeatedly but which also promotes the release of specimen gases during combustion.

SUMMARY OF THE PRESENT INVENTION

The crucible of the present invention satisfies this need by providing a ceramic crucible which can be in the form of a cup-shaped member having an integral floor and a generally cylindrical side wall or a cylindrical member plugged at one end with a suitable material, allowing the sample to be held within the crucible so-defined and having openings to allow gases to pass through the side wall of the crucible. In a preferred embodiment of the invention, the crucible, is made of a porous ceramically-bonded alumina having a mean pore diameter of from about 150 to 350 microns. The porous ceramic crucible is manufactured of a mixture of at least about 92% alumina and about 7.5% silica with trace amounts of titanium dioxide and potassium oxide. The reticulated ceramic crucible so-formed allows gases to pass through the side wall and also allows a number of combustion cycles to be run. Crucibles embodying a preferred embodiment of the invention, therefore, include a floor and have side walls with apertures formed therein which allow the passage of analytical gases through the side wall of the crucible. The material remaining after analysis can successively build up from the floor of the crucible with the unplugged apertures of the crucible side wall above the floor allowing successive combustion cycles until the crucible becomes substantially filled with residue or slag from previous analytical cycles. As can be appreciated, such construction allows a crucible to be used repeatedly as long as sufficient gas flow remains available through the side wall of the crucible. As a result, the cost of each analysis is substantially reduced in view of the ability to successively use the same crucible without replacement. The speed at which analytical cycles can be performed is improved by not having to remove and replace the crucible as frequently.

These and other features, objects and advantages of the present invention will become apparent upon reading the following description thereof together with reference to the accompanying drawings.

BRIEF DESCRIPTION OF THE DRAWINGS

FIG. 1 is a fragmentary side elevational view, partly broken away and in cross section, of an analytical furnace which employs a crucible embodying the present invention;

FIG. 2 is a vertical cross-sectional view of a crucible embodying the present invention;

FIG. 3 is a top plan view of the crucible shown in FIG. 2;

FIG. 4 is a vertical cross-sectional view of an alternative embodiment of the crucible of the present invention; and FIG. 5 is a left-end elevational view of the crucible shown in FIG. 4.

DETAILED DESCRIPTION OF THE PREFERRED EMBODIMENTS

Referring initially to FIG. 1, there is shown a furnace 10 embodying the present invention which includes a generally vertically oriented U-shaped combustion tube 12 defining a combustion chamber 14. The combustion tube 12 is a generally tubular member having a circular cross section and made of suitable quartz or ceramic material. The combustion tube 12 is surrounded by a conventional resistance heater 16 which surrounds the combustion chamber area 14 and can heat the combustion chamber area to temperatures of approximately 1000° C. The resistance heater 16 can be conventional and is well known. The combustion chamber supports a crucible 20 embodying the present invention by means of a crucible support 18 which is porous to allow the gaseous byproducts of combustion to flow through the combustion tube 12 in a direction indicated by arrow A into a reagent section 30 which includes quartz wool plugs 32, 36 between which there is placed a suitable reagent 34, the material of which depends upon the particular analysis as is well known in the art.

A lance tube 38 is positioned above the open mouth 21 of the cup-shaped crucible 20 and directs oxygen or other carrier gas into the crucible for assisting in the combustion of an analytical sample 22 placed on the floor of crucible 20. A sample loading assembly 40 is positioned above the end of combustion chamber 12 and can be of the type described in U.S. Pat. No. 4,573,910, the disclosure of which is incorporated herein by reference. The operation of the sample loading chamber assembly 40 forms no part of the present invention other than to allow successive samples to be dropped within the crucible 20, which can be reused repeatedly due to the gas flow path provided through the side wall of the crucible. The byproducts of combustion travel through the reagent chamber 30 and through a dust trap assembly 50 exiting through conduit 52 to an analyzer.

In the preferred embodiment, the furnace 10 can generally be of the type commercially available from Leco Corporation of St. Joseph, Mich., Model No. 616-197 used in connection with a nitrogen analyzer such as model number 601-500, also known as an FP 528 analyzer. Porous crucible 20, which permits successive usage for multiple analysis is now described in connection with FIGS. 2 and 3.

Crucible 20 comprises a generally cup-shaped member having a disk-shaped floor 24 and an integral cylindrical side wall 26. In the preferred embodiment of the invention, the crucible had an inner diameter of about 0.780" and an outer diameter of about 10.125", thus having a side wall thickness of about 0.1725" and had an overall height of approximately 4". The mean port diameter of the ceramic crucible was approximately 210 microns, although the range of from about 150 to 350 microns is preferred. The porosity of the crucible side wall can be controlled by the manufacture of a crucible employing conventional manufacturing techniques to form the reticulated ceramic material typically utilizing alumina grains to form a slurry with silica and a porcelain cement. The crucible is molded in its green state and, upon firing, provides a matrix of ceramic material having the mean pore diameter of from about 150 to 350 microns determined by the size of the alumina grains. The flow rate of gas through such crucibles provides approximately 13 cubic feet per minute at 150 microns pore diameter, 35 to 45 cubic feet per minute at a 210 micron pore diameter, and of from about 70 to 80 cubic feet per minute at a 350 micron pore diameter at a gas pressure of approximately 40 p.s.i.

The material employed for the crucible comprises a mixture of alumina and silica with trace elements of titanium dioxide and potassium oxide. In the preferred embodiment, the alumina ($Al_2O_3$) was about 92% of the mixture of ceramic material. The silica ($SiO_2$) was about 7.5%, while the titanium dioxide ($TiO_2$) was approximately 0.125% and a trace amount of potassium oxide is also present. The latter two compounds are typical impurities which are found in the alumina and silica materials employed for the manufacture of ceramics. Subsequent to the ceramic slurry being formed typically on a substrate which can be burned away, the ceramic material is pressed into the crucible shape. This green piece crucible is subsequently fired in a conventional manner to remove the substrate material and bond the alumina and silica in an open-pore matrix having a mean pore diameter of from about 150 to 350 microns.

With such a porous crucible as illustrated in FIG. 2, successive analytical samples 22 can be placed within the crucible supported by floor 24 and the side wall 26 provides a passage for gases of combustion therethrough for a considerable number of cycles of analysis which results in a successive build-up layer 22' of ash or slag from the original sample until the crucible floor and side wall are substantially clogged so that no further passage of combustion byproducts is feasible. With such crucibles, the number of analysis can range from about 100 to 500 depending upon the size of the specimen and the nature of its byproducts of combustion. Thus, crucibles which are configured to have apertures through the side walls, preferably in the form of interstitial spaces, but which could also be in the nature of slots, small apertures or other passageways formed through the side wall of the crucible, permit the crucible to be used for multiple analyses. Also, other materials, such as quartz or high temperature alloys, may be employed.

Instead of the cup-shaped crucible 20 show in FIGS. 1–3, a crucible 60 shown in FIGS. 4 and 5 can also be employed. The crucible 60 is a cylindrical ceramic sleeve made of the same material and by the same process as the cup-shaped crucible 20 shown in FIGS. 2 and 3, however, it has both an open mouth 61 for receiving a sample therein as well as a carrier gas and supports a sample 22 in the center side wall 62 area of the crucible. The opposite end 63 of crucible 60 is plugged by an alumina powder disk 70 having a thickness of approximately 1/8" behind which there is placed a quartz wool 72 having a thickness of approximately 1/2". The overall length of crucible 70 is approximately 4", and it has an inner diameter of about 0.78" and an outer diameter of about 1.125", providing a wall thickness of about 0.1725". Gas flow in crucible 60 can be through both the side wall, as indicated by arrow B in FIG. 4, as well as through end 63 as indicated by arrow C. Typically, crucible 60 will be used with a horizontally oriented combustion chamber as opposed to the vertically oriented chamber as shown in FIG. 1 and, like crucible 20, has a porosity with a pore diameter from about 150 to 350 microns to allow such passage of gaseous byproducts of combustion.

Thus, with either crucible 20 or 60, the crucibles may be used repeatedly until such tire as the pores or apertures formed through the side wall of the crucibles have become clogged with residue. Such construction, therefore, reduces the cost of running samples and permits the analysis of multiple samples without the need for removing and replacing crucibles on a frequent basis.

It will become apparent to those skilled in the art that various modifications to the preferred embodiments of the invention as described herein can be made without departing from the spirit or scope of the invention as defined by the appended claims.

The invention claimed is:

1. An analytical crucible comprising:

a cup-shaped crucible made of a porous ceramic material having a cylindrical side wall, said crucible having a porosity defined by a pore diameter of from about 150 to about 350 microns for allowing the escape of gaseous byproducts of combustion along and through said cylindrical side wall of said crucible for successive analyses.

2. The crucible as defined in claim 1 wherein said ceramic material includes alumina and silica.

3. The crucible as defined in claim 2 wherein said ceramic material comprises about 92% alumina and about 7.5% silica.

4. The crucible as defined in claim 3 wherein said cup-shaped crucible comprises a disk-shaped floor and said cylindrical side wall is integrally formed with said floor.

5. The crucible as defined in claim 1 wherein the porosity of said ceramic material provides a flow rate through said side wall of from about 13 cubic feet per minute to about 80 cubic feet per minute at a pressure of about 40 psi.

6. An analytical crucible comprising:

a cup-shaped ceramic crucible having a side wall having porous openings along the entire side wall for allowing the escape of gaseous byproducts of combustion through said side wall, wherein said ceramic material has a pore diameter of from about 150 to about 350 microns.

7. The crucible as defined in claim 6 wherein said ceramic material includes alumina and silica.

8. The crucible as defined in claim 7 wherein said ceramic material comprises about 92% alumina and about 7.5% silica.

9. The crucible as defined in claim 8 wherein said cup-shaped crucible comprises a disk-shaped floor having an integral generally cylindrical side wall.

10. An analytical crucible comprising:

a cylindrical crucible having a side wall made of a porous ceramic material with a porosity defined by a pore diameter of from about 150 to about 350 microns for allowing the escape of gaseous byproducts of combustion through said side wall.

11. The crucible as defined in claim 10 wherein one end of said cylindrical crucible is enclosed by a porous plug.

12. The crucible as defined in claim 11 wherein said ceramic material includes alumina and silica.

13. The crucible as defined in claim 12 wherein said ceramic material comprises about 92% alumina and about 7.5% silica.

14. An analytical crucible comprising:

a sample supporting crucible having a wall with porous openings therethrough having a diameter of from about 150 to about 300 microns for allowing the escape of gaseous byproducts of combustion through said wall.

15. The crucible as defined in claim 14 wherein said crucible wall is a side wall.

16. The crucible as defined in claim 15 wherein said crucible is generally cup-shaped.

17. The crucible as defined in claim 16 wherein said crucible is made of a porous ceramic material.

* * * * *

UNITED STATES PATENT AND TRADEMARK OFFICE
CERTIFICATE OF CORRECTION

PATENT NO.    : 6,270,727 B1                                                          Page 1 of 1
DATED         : August 7, 2001
INVENTOR(S)   : Mitchell et al.

It is certified that error appears in the above-identified patent and that said Letters Patent is hereby corrected as shown below:

<u>Column 2,</u>
Line 65, "10.125" " should be -- 1.125" --.

<u>Column 4,</u>
Line 7, "tire" should be -- time --.

Signed and Sealed this

Second Day of July, 2002

Attest:

Attesting Officer

JAMES E. ROGAN
*Director of the United States Patent and Trademark Office*